US00PP23456P2

(12) United States Plant Patent
Zlesak

(10) Patent No.: US PP23,456 P2
(45) Date of Patent: Mar. 12, 2013

(54) POLYANTHA ROSE PLANT NAMED 'ZLECHARLIE'

(50) Latin Name: *Rosa hybrida*
Varietal Denomination: ZLECharlie

(76) Inventor: David Charles Zlesak, St. Paul, MN (US)

( * ) Notice: Subject to any disclaimer, the term of this patent is extended or adjusted under 35 U.S.C. 154(b) by 0 days.

(21) Appl. No.: 13/317,910

(22) Filed: Nov. 1, 2011

(51) Int. Cl.
*A01H 5/00* (2006.01)

(52) U.S. Cl. ..... Plt./143
(58) Field of Classification Search ..... Plt./143
See application file for complete search history.

*Primary Examiner* — Annette Para

(57) ABSTRACT

Polyantha rose plant having a mounded, well-branched, compact plant habit; vigorous growth; single flowers typically borne in clusters of 6 or more; multicolored petals having magenta-pink edges and white petal bases; continuous flowering throughout the growing season; resistance to major fungal diseases; stems that are nearly free of prickles and ability to root and grow vigorously from softwood and semi-hardwood cuttings.

4 Drawing Sheets

Latin name of the plant claimed: *Rosa hybrida.*
Variety denomination: 'ZLECharlie'.

BACKGROUND OF THE INVENTION

The primary objective of making this cross was to produce a new rose variety having the vigorous growth, mounded plant form, continuous blooming habit, and attractive flower form of the female parent and the attractive petal color and winter hardiness of the male parent. The pollination occurred in late spring 2004. Seed from this cross germinated during the winter of 2004/2005 and 'ZLECharlie' was identified as a superior seedling and was first asexually propagated during the summer of 2005.

The present invention relates to a new and distinct variety of rose plant of the polyantha commercial class designated 'ZLECharlie'. 'ZLECharlie' was originated by me by crossing two of my unnamed, unreleased seedling selections. The female parent of 'ZLECharlie' is a seedling selection designated 2002-22 and the male parent is a selection designated Poly A.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Mounded, well-branched, compact plant habit;
2. Vigorous growth;
3. Single flowers typically borne in clusters of 6 or more;
4. Multicolored petals having magenta-pink edges and white petal bases;
5. Continuous flowering throughout the growing season;
6. Resistance to major fungal diseases;
8. Stems that are nearly free of prickles:
7. Ability to root and grow vigorously from softwood and semi-hardwood cuttings.

Asexual reproduction of this new variety by rooting softwood and semi-hardwood cuttings, as performed at St. Paul, Minn., shows that the foregoing and all other characteristics and distinctions come true to form and are established and transmitted through succeeding generations of asexual propagation.

COMPARISON WITH PARENTS

'ZLECharlie' has relatively large single flowers (five petals per flower) for a rose of the polyantha commercial class and a mounded, well-branched, compact habit and differs from its female parent, 2002-22, in that 2002-22 has double light pink blooms (over 20 petals per flower) and is less cold hardy (plants of 2002-22 have died over winter due to cold in United States Department of Agriculture cold hardiness zone 4). 'ZLECharlie' differs from its male parent, Poly A, in that Poly A has smaller flowers and leaves. Poly A shares key traits with 'ZLECharlie' in that they both have single flowers with magenta-pink edges. Both Poly A and 'ZLECharlie' have been consistently winter hardy in United States Department of Agriculture cold hardiness zone 4. 'ZLECharlie', 2002-22, and Poly A all have near prickle-free stems.

COMPARISON WITH SIMILAR VARIETY

The rose variety with the greatest similarity to 'ZLECharlie' is 'Lena' (marketed under the name Northern Accents™ Lena; not patented in the United States), a rose designated as a member of the shrub commercial class. Both 'ZLECharlie' and 'Lena' have single blooms with petals that have both pink and white coloration and relatively compact, mounded plants. 'ZLECharlie' has blooms that are slightly larger with a deeper magenta-pink margin and stems with fewer prickles than 'Lena'.

BRIEF DESCRIPTION OF THE DRAWINGS

The accompanying illustration shows typical specimens of the vegetative growth, flowers, and hips of this new variety in different stages of development, depicted in color as true as it is reasonably possible.

DETAILED BOTANICAL DESCRIPTION

Figure 1:
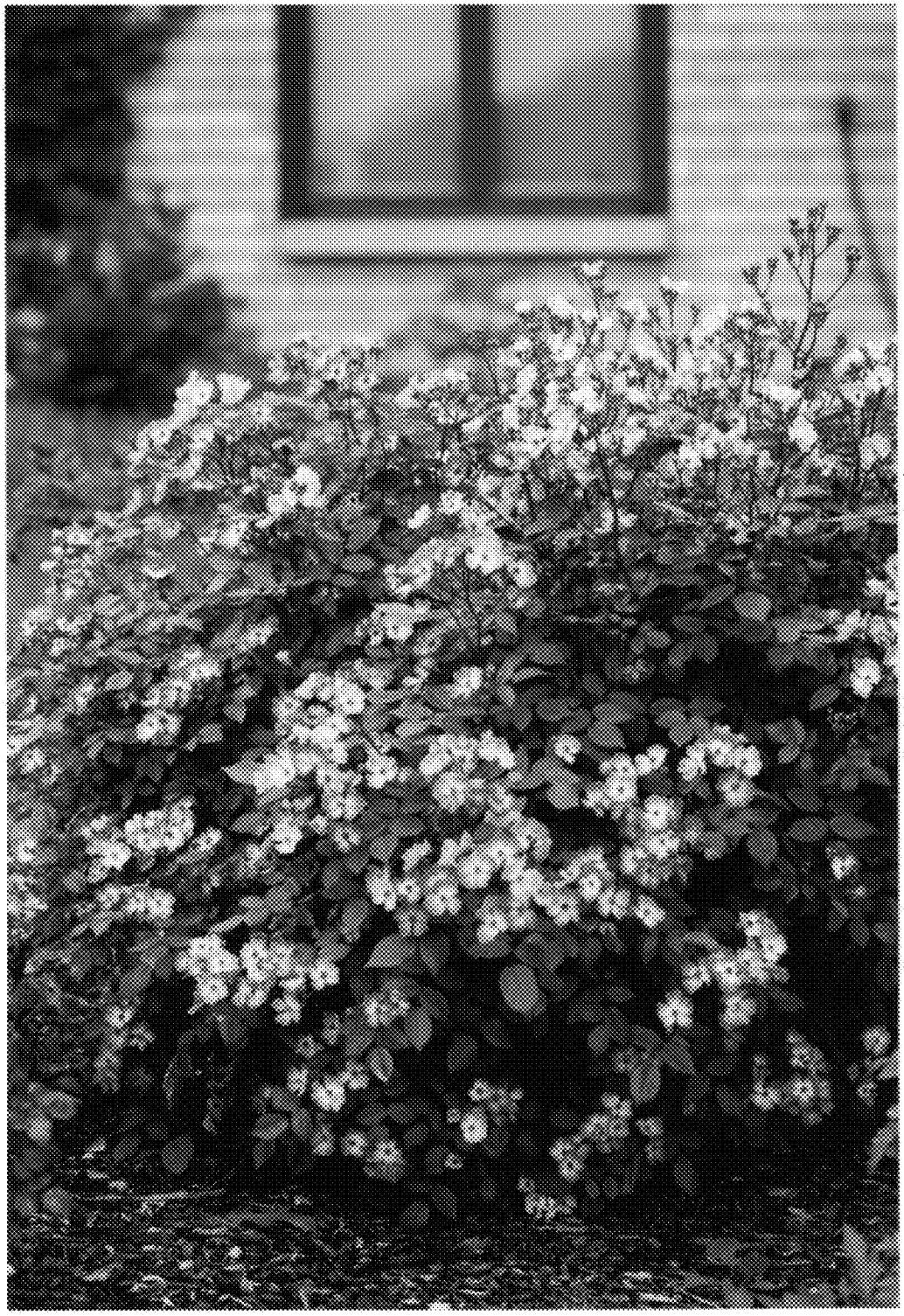
FIG. 1 illustrates a mature plant growing in a landscape.
Figure 2:
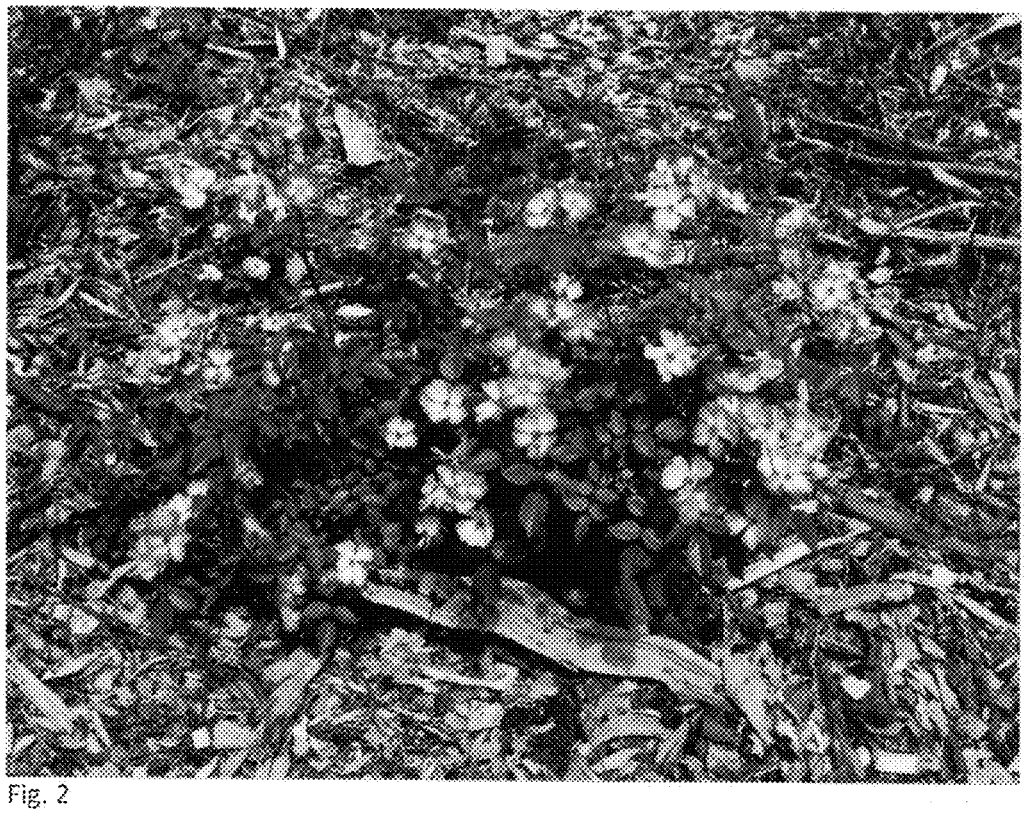
FIG. 2 illustrates an immature plant growing in a landscape.
Figure 3:
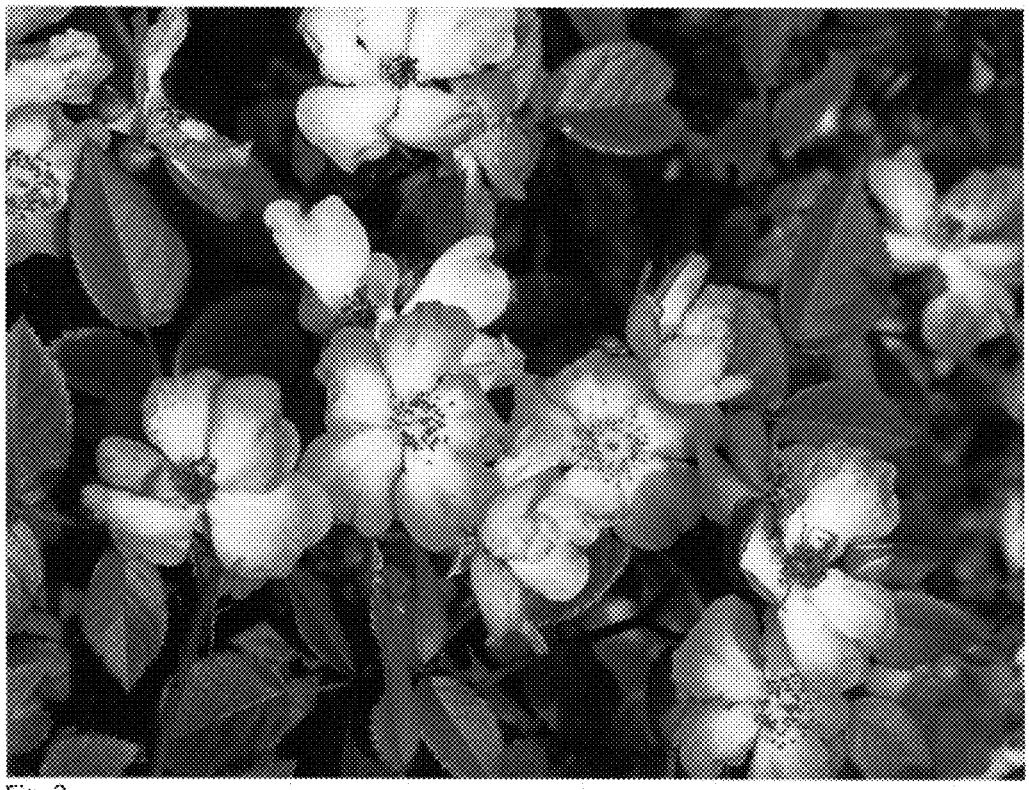
FIG. 3 illustrates a close up view of a group of flowers at different stages of development.
Figure 4:
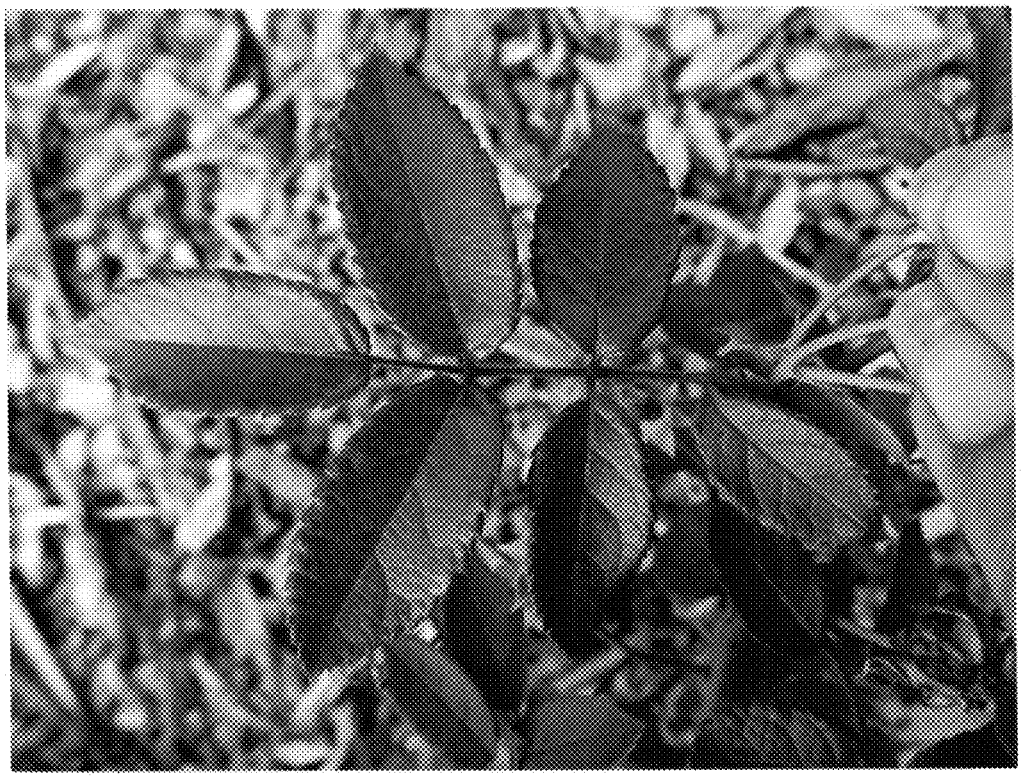
FIG. 4 illustrates a leaf.
Figure 5:
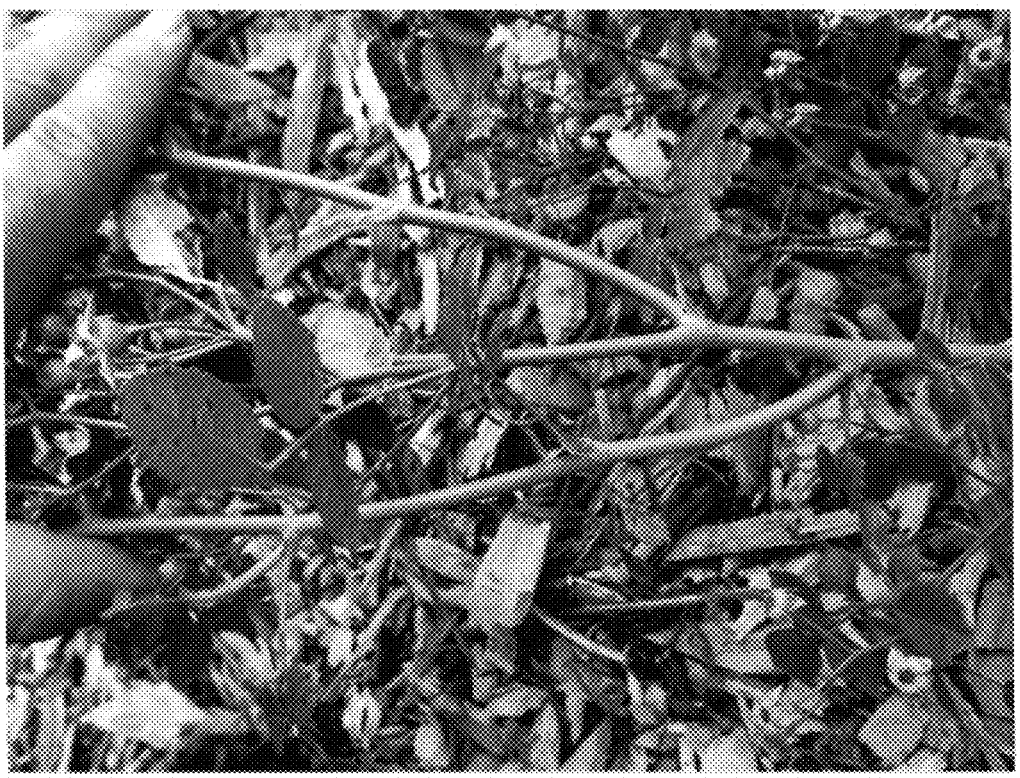
FIG. 5 illustrates stems without prickles.
Figure 6:
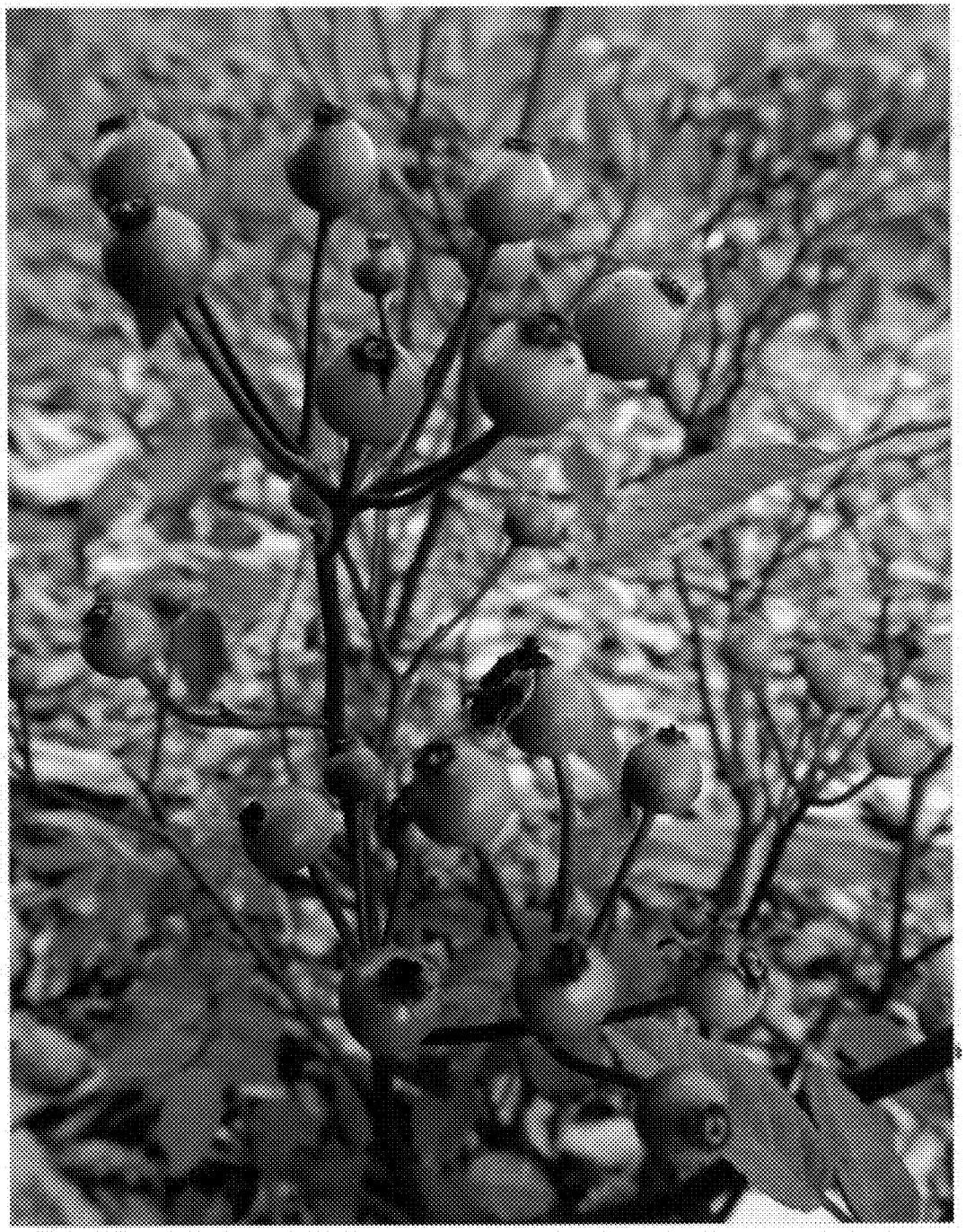
FIG. 6 illustrates ripe and ripening hips.

The following is a detailed description of my new rose cultivar with color descriptions using terminology in accordance with The Royal Horticultural Society (London) Colour Chart (2001), except where ordinary dictionary significance of color is indicated. The phenotype of the new cultivar may vary with variations in environmental, climatic, and cultural conditions, as it has not been tested under all possible environmental conditions. Descriptions are based on observations of plants approximately five years of age that were propagated from semi-hardwood cuttings.

Parentage:

*Seed parent*.—An unnamed seedling never released for sale of the polyantha commercial rose class from my breeding program, which I designate as 2002-22. 2002-22 results from open-pollination of a seedling from the cross of *Rosa setigera*×an unnamed polyantha seedling from my breeding program designated as 95-1.

*Pollen parent*.—An unnamed seedling never released for sale of the polyantha commercial rose class from my breeding program, which I designate as Poly A. Poly A is the result of two generations of open-pollination of an unnamed polyantha seedling from my breeding program designated as 95-1.

Classification:

*Botanical*.—*Rosa hybrida*.

*Commercial*.—Polyantha.

Flower:

*Blooming habit*.—Continuous throughout the growing season.

Flower bud:

*Size*.—10-12 mm long and 6-7 mm in diameter when the petals start to unfurl.

*Form*.—The bud form is ovoid and pointed.

*Color*.—When sepals first divide, visible petal color is Red-Purple Group N66A. When half blown, the upper or adaxial sides of the petals are closest to Red-Purple Group N66B on the distal end (comprising one half to two thirds of the overall petal surface) and white (closest to White Group 155D) at the proximal end (one third to one half of the petal surface). The lower, or abaxial, sides of the petals are Red-Purple Group 67D at the distal end and the color blends gradually to White Group 155D at the proximal end.

*Sepals*.—Color: Yellow-Green Group 146B on the abaxial side and Green Group 138C on the adaxial side. Length: 8-10 mm. Width: 4-5 mm. Shape: ovate to oblong with acuminate tips. Surface texture: Adaxial, Hoary. Abaxial, Generally smooth with some very small glandular hairs. There are three lightly appendaged sepals. There are two unappendaged sepals which have hoary edges.

*Receptacle*.—Color: Yellow-Green Group 146C. Shape: round to slightly elliptic. Size: Small, about 3-4 mm wide and 3-4 mm long. Surface: glabrous.

*Peduncle*.—Length: Medium, averaging about 12-22 mm. Width: Medium, averaging 2 mm. Surface: Generally glabrous with some very small glandulous hairs. Color: Yellow-Green Group 146D. Strength: Stiff, primarily erect.

Bloom:

*Size*.—Medium to large for the polyantha commercial class. Typical open diameter is 30-40 mm.

*Borne*.—Typically clusters of 6-20 blooms are borne at the end of stems in an inflorescence type that varies between a panicle and a corymb (a shortened panicle that can be somewhat domed at the terminal).

*Form*.—When blooms first open: Slightly cupped to flat. Petals typically have slightly undulating edges.

*Fragrance*.—Slight. Character of fragrance: Spicy.

*Permanence*.—Blooms retain their form to the end.

*Petalage*.—Typically 5.

*Petal color*.—The adaxial sides of the petals are primarily Purple-Red Group N66C throughout the distal one third to one half of the petal surface and bright white (closest color in the before mentioned Colour Chart is White Group 155D) at the base or proximal half to two thirds of the petal. The color of the abaxial side of the petals is primarily Purple-Red Group N66D at the distal quarter of the petal surface and slowly blends to bright white (closest color in the before mentioned Colour Chart is White Group 155D) at the proximal end of the petal.

*Petal discoloration*.—The general tonality of the adaxial petal distal edge surface of a fully open bloom at the first day through the second day: Purple-Red Group N66C. The general tonality of the adaxial petal surface at day six: between Violet Group 84C and Pink Group 75B. The distal quarter of the abaxial surface of the petal is Purple-Red Group N66D typically for the first two days and then gradually fades to Pink Group 75C by day six and the proximal end of the petal is bright white (closest color in the before mentioned Colour Chart is White Group 155D) throughout the duration of the bloom.

*Petal texture*.—Thick and satiny to the touch.

*Petal length*.—1.4-1.7 cm.

*Petal width*.—1.2-1.6 cm.

*Petal shape*.—Obcordate.

*Petal margin*.—Entire to slightly undulating.

*Petal apex shape*.—Obcordate and sometimes petals possess a small point in the axis.

*Petal base shape*.—Cuneate.

*Petal form*.—Flat to slightly cupped with often undulating margins.

*Arrangement*.—One row of slightly overlapping petals.

*Petaloids*.—Typically none.

*Persistence*.—Petals drop off cleanly before drying.

*Lastingness*.—On the plant: Medium (about 6-8 days). As a cut flower: Medium (about 6 days).

Reproductive organs:

*Stamens*.—Number per flower: 60-80. Anthers — Size: Length before dehiscence: 1.0 mm, Width before dehiscence: 1.0 mm. Length after dehiscence: 0.5 mm. Width after dehiscence: 0.5 mm. Color: Before dehiscense: Yellow Orange Group 17A. After dehiscence: Yellow-Orange Group 22A. Arrangement: Regular and borne around styles. Filaments — Size: Length: 3-7 mm. Width: 0.25 mm. Color: White Group 155D. Pollen — Color: Yellow Orange Group 17A.

*Pistils*.—Number per flower: 8-15. Styles — Color: Red Group 51C. Length: 3-5 mm. Stigmas — Color: Yellow-Green Group 145A. Ovary — Color of immature ovary: Yellow-Green Group 145D.

*Hips*.—The fleshy portion of rose hips is comprised of hypanthium tissue and inside that tissue are achenes — individual indehiscent fruits that contain a single embryo within the hard paricarp. Hips are typically abundantly produced on 'ZLECharlie'. Sepals typically abscise upon ripening. Hypanthium: Color when immature: Green Group 146C. Color when mature: Orange-Red Group 30B. Shape: Generally round. Size: 10-12 mm long and 10-12 mm wide.

*Achenes* (*ripe*).—Color: Yellow Green Group 150D. Shape: Irregular. Size: 4-6 mm. Typically there are 6-8 achenes per hip.

Plant:

*Form*.—Rounded shrub.

*Growth*.—Very vigorous, well-branched, and dense.

*Age at maturity*.—3 years.

*Mature plant*.—Height and width typically are both about 60 cm.

Leaf:

*Form*.—Leaves typically have five to seven leaflets.

*Arrangement*.—Leaves are alternately arranged on stems.

*Size*.—Medium (10 cm long and 7 cm wide).

*Quantity*.—Normal.

*Leaflet color*.—New foliage: Adaxial side: Yellow-Green Group 146A. Abaxial side: Yellow Green Group 146C. Mature foliage: Adaxial side: Green Group 137B. Abaxial side: Yellow-Green Group 146B.

*Leaflet veination pattern*.—Pinnate reticulate.

*Leaflet veination color*.—The color of the veins is the same or very close to that of the overall leaf blade. New foliage: Adaxial side: Yellow-Green Group 146A. Abaxial side: Yellow Green Group 146C. Mature foliage: Adaxial side: Green Group 137B. Abaxial side: Yellow-Green Group 146B.

*Leaflet size*.—Terminal leaflets: Medium (3.5-4.0 cm long and 2.0-2.5 cm wide). Non-terminal leaflets: Medium (3.5-4.0 cm long and 2.0-2.5 cm wide).

*Leaflet shape*.—Elliptic.

*Leaflet base shape*.—Obtuse.

*Leaflet apex shape*.—Typically acute and in some instances slightly acuminate.

*Leaflet texture*.—Semi-glossy, rugose. On the adaxial side of leaflets the veins are slightly recessed and on the abaxial side they are slightly elevated relative to the general leaf blade.

*Leaflet edge*.—Serrated.

*Petiole*.—Color — Yellow-Green Group 146C.

*Petiole rachis*.—Color: Yellow-Green Group 146C.

*Petiole underside*.—Generally smooth with periodic small prickles that are about 0.5 mm long and 0.1 to 0.2 mm wide and Yellow-Green Group 146C in color.

*Stipules*.—Short (about 1.1-1.5 cm in length and 0.3-0.5 cm in width). Color: Yellow-Green Group 146A, edges with several relatively parallel and very narrow appendages (0.3-1.0 mm long and 0.1 mm wide).

*Disease resistance*.—Resistant to powdery mildew, black spot, and rust under normal growing conditions.

*Pest persistence*.—Not observed.

Stems:

*Strength*.—Strong.

*Length*.—Typically about 20-35 cm.

*Diameter*.—Varies and is most commonly 4-6 mm. Larger stems arising from the base of the plant are about 0.8-1.0 cm in diameter, while smaller stems arising from either the base of the plant or secondary or tertiary stems arising within the plant canopy are commonly 3-5 mm in diameter.

*Color*.—New stems: Generally Yellow-Green Group 146C. Bark: Smooth. Mature stems: Yellow-Green Group 146B. Bark: Smooth.

Stem prickles:

*Quantity*.—Typically none, but periodically some are produced.

*Form*.—Straight to very slightly downward hooked.

*Length*.—6-8 mm.

*Width*.—0.5 cm near stem and narrowing to tip.

*Color when young*.—Yellow-Green Group 146D often with some overlaid red color in the sun of Greyed-Red Group 178C.

*Color when mature*.—Greyed-Yellow Group 161C.

*Secondary stem prickles*.—None.

Cytology:

*Ploidy*.—Diploid (2n=2x=14). Meristematic root tip cells in the stage of metaphase of mitosis were observed to have 14 chromosomes under a light microscope at 400× magnification.

Winter hardiness: Consistently crown hardy to United States Department of Agriculture cold hardiness zone 4.

I claim:

1. A new and distinct variety of rose plant of the polyantha class, substantially as herein shown and described, characterized particularly by its mounded, well-branched, compact plant habit; vigorous growth; single flowers typically borne in clusters of 6 or more; multicolored petals having magenta-pink edges and white petal bases; continuous flowering throughout the growing season; resistance to major fungal diseases; stems that are nearly free of prickles and ability to root and grow vigorously from softwood and semi-hardwood cuttings.

* * * * *